US010436750B2

(12) United States Patent
Shinada et al.

(10) Patent No.: US 10,436,750 B2
(45) Date of Patent: Oct. 8, 2019

(54) DIELECTRIC BARRIER DISCHARGE IONIZATION DETECTOR

(71) Applicants: Shimadzu Corporation, Kyoto (JP); Osaka University, Osaka (JP)

(72) Inventors: Kei Shinada, Kyoto (JP); Katsuhisa Kitano, Osaka (JP)

(73) Assignees: Shimadzu Corporation, Kyoto (JP); Osaka University, Osaka (JP)

(*) Notice: Subject to any disclaimer, the term of this patent is extended or adjusted under 35 U.S.C. 154(b) by 0 days.

(21) Appl. No.: 15/698,312

(22) Filed: Sep. 7, 2017

(65) Prior Publication Data

US 2018/0067079 A1    Mar. 8, 2018

(30) Foreign Application Priority Data

Sep. 8, 2016  (JP) .................................. 2016-175504

(51) Int. Cl.
    *G01N 27/68*    (2006.01)
    *G01N 27/66*    (2006.01)
    (Continued)

(52) U.S. Cl.
    CPC ............. *G01N 27/68* (2013.01); *G01N 27/66* (2013.01); *G01N 30/64* (2013.01);
    (Continued)

(58) Field of Classification Search
    CPC .... G01N 27/68; G01N 30/64; G01N 33/0027; G01N 27/66; G01N 2030/025;
    (Continued)

(56) References Cited

U.S. PATENT DOCUMENTS

| 4,282,521 A | 8/1981 | Lieberman |
| 6,489,585 B1 | 12/2002 | Nakamura et al. |

(Continued)

FOREIGN PATENT DOCUMENTS

| CN | 102368060 A | 3/2012 |
| CN | 102866224 A | 1/2013 |

(Continued)

OTHER PUBLICATIONS

Kogelschatz, Dielectric-barrier Discharges: Their History, Discharge Physics, and Industrial Applications, Plasma Chemistry and Plasma Processing, vol. 23, No. 1, Mar. 2003.*

(Continued)

*Primary Examiner* — Daniel R Miller
(74) *Attorney, Agent, or Firm* — Maier & Maier, PLLC

(57) ABSTRACT

The dielectric barrier discharge ionization detector includes: a dielectric tube through which a plasma generation gas is passed; a high-voltage electrode formed on the outer wall of the dielectric tube; two ground electrodes and formed on the outer wall of the dielectric tube, with the high-voltage electrode in between; a voltage supplier for applying AC voltage between the high-voltage electrode and each ground electrode to generate electric discharge within the dielectric tube and thereby generate plasma from the plasma generation gas; and a charge-collecting section for detecting an ion current formed by ionized sample-component gas produced by the plasma. The distance between one ground electrode and the high-voltage electrode is longer than a discharge initiation distance between these two electrodes, while the distance between the other ground electrode and the high-voltage electrode is shorter than the discharge initiation distance between these two electrodes.

4 Claims, 6 Drawing Sheets

(51) Int. Cl.
  *G01N 30/64* (2006.01)
  *G01N 33/00* (2006.01)
  *H05H 1/00* (2006.01)
  *H05H 1/24* (2006.01)
  G01N 30/02 (2006.01)
  G01R 19/00 (2006.01)

(52) U.S. Cl.
  CPC ....... *G01N 33/0027* (2013.01); *H05H 1/0006* (2013.01); *H05H 1/0081* (2013.01); *H05H 1/2406* (2013.01); *G01N 2030/025* (2013.01); *G01N 2030/647* (2013.01); *G01R 19/0061* (2013.01); *H05H 2001/2443* (2013.01)

(58) Field of Classification Search
  CPC .. H05H 1/2406; H05H 1/0081; H05H 1/0006; H05H 2001/2443; G01R 19/0061
  See application file for complete search history.

(56) References Cited

U.S. PATENT DOCUMENTS

| | | |
|---|---|---|
| 2009/0236042 A1 | 9/2009 | Wada et al. |
| 2010/0320916 A1 | 12/2010 | Yagi et al. |
| 2011/0168881 A1 | 7/2011 | Sturgeon et al. |
| 2011/0260732 A1* | 10/2011 | Shinada ................ G01N 27/70 324/464 |
| 2011/0316552 A1 | 12/2011 | Shinada et al. |
| 2013/0154658 A1 | 6/2013 | Shinada et al. |
| 2014/0145724 A1 | 5/2014 | Shinada et al. |
| 2015/0369777 A1* | 12/2015 | Shinada ................ G01N 30/64 324/464 |
| 2017/0292904 A1 | 10/2017 | Xing et al. |
| 2018/0067080 A1 | 3/2018 | Shinada et al. |
| 2018/0067081 A1 | 3/2018 | Shinada et al. |
| 2018/0067082 A1 | 3/2018 | Shinada et al. |
| 2018/0067083 A1 | 3/2018 | Shinada et al. |

FOREIGN PATENT DOCUMENTS

| | | |
|---|---|---|
| JP | 2010-060354 A | 3/2010 |
| JP | 2013-125022 A | 6/2013 |
| WO | 2012/169419 A1 | 12/2012 |

OTHER PUBLICATIONS

Shinada et al., "Development of New Ionization Detector for Gas Chromatography by Applying Dielectric Barrier Discharge", Shimadzu Flyouron (Shimadzu Review), vol. 69, Nos. 3/4, Mar. 29, 2013, pp. 255-263.

Notice of Allowance dated Oct. 17, 2018 in corresponding U.S. Appl. No. 15/698,391; 13 pages.

Office Action dated Nov. 1, 2018 in corresponding U.S. Appl. No. 15/698,351; 12 pages.

Notice of Allowance dated Jun. 25, 2019 in corresponding U.S. Appl. No. 15/698,368; 13 pages.

Office Action dated Jun. 14, 2019 in corresponding U.S. Appl. No. 15/698,331; 20 pages.

Office Action dated May 28, 2019, in corresponding Chinese Application No. 201710798481.9 including partial machine-generated English-language translation; 9 pages.

Office Action dated Jun. 11, 2019, in corresponding U.S. Appl. No. 15/698,351; 12 pages.

* cited by examiner

DIELECTRIC BARRIER DISCHARGE IONIZATION DETECTOR

TECHNICAL FIELD

The present invention relates to a dielectric barrier discharge ionization detector which is primarily suitable as a detector for a gas chromatograph (GC).

BACKGROUND ART

In recent years, dielectric barrier discharge ionization detectors (which are hereinafter abbreviated as the "BIDs") employing the ionization by dielectric barrier discharge plasma have been put to practical use as a new type of detector for GC (for example, see Patent Literatures 1 and 2 as well as Non Patent Literature 1).

BIDs described in the aforementioned documents are roughly composed of a discharging section and a charge-collecting section which is located below the discharging section. In the discharging section, a low-frequency AC high voltage is applied to plasma-generating electrodes circumferentially formed around a tube made of a dielectric material, such as quartz glass ("dielectric tube"), to ionize an inert gas supplied into the tube line of the dielectric tube and thereby form atmospheric-pressure non-equilibrium plasma. Due to the effects of the light emitted from this plasma (vacuum ultraviolet light), excited species and other elements, the sample components in a sample gas introduced into the charge-collecting section are ionized. The resulting ions are collected through a collecting electrode to generate detection signals corresponding to the amount of ions, i.e. the amount of sample components.

FIG. 7 shows the configuration of the discharging section and surrounding area in the aforementioned BID. As noted earlier, the discharging section 610 includes a cylindrical dielectric tube 611 made of a dielectric material, such as quartz, the inner space of which forms a passage of inert gas, such as helium (He) or argon (Ar) gas. On the outer wall surface of the cylindrical dielectric tube 611, three ring-shaped metallic electrodes (made of stainless steel, copper or the like) are circumferentially formed at predetermined intervals of space. A high AC excitation voltage power source 615 for generating a low-frequency high AC voltage is connected to the central electrode 612 among the three electrodes, while the electrodes 613 and 614 located above and below the central electrode are both grounded. Hereinafter, the central electrode is called the "high-voltage electrode" 612, while the upper and lower electrodes are called the "ground electrodes" 613 and 614. The three electrodes are collectively referred to as the plasma generation electrodes. Since the wall surface of the cylindrical dielectric tube 611 is present between the passage of the inert gas and the plasma generation electrodes 612, 613 and 614, the dielectric wall itself functions as a dielectric coating layer which covers the surface of those electrodes 612, 613 and 614, enabling dielectric barrier discharge to occur. With the inert gas flowing through the cylindrical dielectric tube 611, when the high AC excitation voltage power source 615 is energized, a low-frequency high AC voltage is applied between the high-voltage electrode 612 and each of the upper and lower ground electrodes 613 and 614 located above and below. Consequently, an electric discharge occurs within the area sandwiched between the two ground electrodes 613 and 614. This electric discharge is induced through the dielectric coating layer (the wall surface of the cylindrical dielectric tube 611), and therefore, is a form of dielectric barrier discharge, whereby the inert gas (plasma generation gas) flowing through the cylindrical dielectric tube 611 is ionized over a wide area, forming a cloud of plasma (atmospheric-pressure non-equilibrium plasma).

In the BID configured in the previously described manner, the dielectric layer which covers the surface of the plasma generation electrodes prevents an emission of thermions or secondary electrons from the surface of the metallic electrodes. Furthermore, since the plasma generated by the dielectric barrier discharge is a non-equilibrium plasma with low-temperature neutral gas, various factors which cause a fluctuation of the plasma are suppressed, such as a temperature fluctuation in the discharging section or an emission of gas from the inner wall of the quartz tube due to the heat. As a result, the BID can maintain plasma in a stable form and thereby achieve a higher level of signal-to-noise ratio than the flame ionization detector (FID), which is the most commonly used type of detector for GC.

CITATION LIST

Patent Literature

Patent Literature 1: JP 2010-60354 A
Patent Literature 2: WO 2012/169419 A

Non Patent Literature

Non Patent Literature 1: Shinada and four other authors, "Development of New Ionization Detector for Gas Chromatography by Applying Dielectric Barrier Discharge", *Shimadzu Hyouron* (*Shimadzu Review*), Vol. 69, Nos. 3/4, Mar. 29, 2013

SUMMARY OF INVENTION

Technical Problem

As already explained, the BID configured in the previously described manner has two ground electrodes 613 and 614 arranged so as to sandwich the high-voltage electrode 612 in between. This arrangement prevents the plasma generated by the electric discharge from spreading into the upstream and downstream sections of the cylindrical dielectric tube 611, whereby the effective plasma generation area is confined to the space between the two ground electrodes 613 and 614.

However, in the BID having such a configuration, the detection output may become unstable depending on the operating conditions of the BID, such as the frequency and amplitude of the low-frequency AC voltage applied between the high-voltage electrode and the ground electrodes. FIG. 8 shows one example of the detection output in such a situation. The figure shows the detection output (output baseline) of the BID recorded when no sample gas was introduced. When no sample gas is introduced, the detection output should be at an approximately constant level, whereas the detection output shown in the figure is alternating between high and low baseline levels.

The present invention has been developed in view of such a point. Its objective is to improve the stability of the detection output in a BID having a configuration in which a high-voltage electrode and two ground electrodes are circumferentially formed on the outer circumferential surface of a dielectric tube, with the high-voltage electrode located between the ground electrodes.

Solution to Problem

The present inventors have searched for the cause of the previously described destabilization of the detection output and discovered that, when the detection output was unstable, the generation area of the electric discharge was alternating between the upstream and downstream regions across the boundary area where the high-voltage electrode was located. This vertical switching of the discharge generation area within the dielectric tube would cause a corresponding vertical switching of the plasma generation area, which would consequently change the amount of vacuum ultraviolet light or excited species originating from the plasma and reaching the charge-collecting section. This seemed to be the cause of the destabilization of the detection output. Based on this finding, the present inventors have conducted exhaustive research on methods for preventing the switching of the discharge generation area to stabilize the detection output, and completed the present invention.

That is to say, the dielectric barrier discharge ionization detector according to the present invention developed for solving the previously described problem includes:

a) a dielectric tube containing one section of a gas passage through which a plasma generation gas is passed;

b) a high-voltage electrode circumferentially formed on the outer wall of the dielectric tube;

c) two ground electrodes electrically grounded and circumferentially formed on the outer wall of the dielectric tube at positions between which the high-voltage electrode is located;

d) a voltage supplier connected to the high-voltage electrode, for applying an AC voltage between the high-voltage electrode and each of the two ground electrodes so as to generate an electric discharge within the dielectric tube and thereby generate plasma from the plasma generation gas; and e) a charge-collecting section forming a section of the gas passage located downstream of the generation area of the plasma, including a sample-gas introducer for introducing a sample gas into the downstream section and a collecting electrode for collecting ions generated from a sample component in the sample gas by light emitted from the plasma, where the distance between one ground electrode of the two ground electrodes and the high-voltage electrode is longer than a discharge initiation distance between these two electrodes, while the distance between the other ground electrode and the high-voltage electrode is shorter than a discharge initiation distance between these two electrodes.

According to this configuration, during the voltage-applying operation by the voltage supplier, no electric discharge occurs within the area between the one ground electrode and the high-voltage electrode, whereas an electric discharge always occurs within the area between the other ground electrode and the high-voltage electrode. Therefore, unlike the conventional BID, no alternate switching of the discharge generation area and plasma generation area occurs between the upstream and downstream regions across the high-voltage electrode, and a stable detection output is obtained. It should be noted that the one ground electrode (i.e. the electrode which does not contribute to the electric discharge) still has the function of preventing the plasma generation area from spreading within the dielectric tube in the previously described manner.

The "discharge initiation distance" depends on such parameters as the frequency and amplitude of the AC voltage applied from the voltage supplier, kind and concentration of the plasma generation gas, as well as the dielectric material forming the dielectric tube. Therefore, the "distance between one ground electrode and the high-voltage electrode" in the present invention should be adjusted according to those parameters so that no electric discharge will occur between the one ground electrode and the high-voltage electrode. The "distance between the other ground electrode and the high-voltage electrode" in the present invention should also be adjusted according to those parameters so that an electric discharge can occur between the other ground electrode and the high-voltage electrode.

The present invention can suppress the destabilization of the detection output even when the ground electrode located on the upstream side of the high-voltage electrode is used as the "one" electrode (i.e. when the distance between the upstream-side ground electrode and the high-voltage electrode is made to be longer than the discharge initiation distance). However, it is more preferable to make the distance between the downstream-side ground electrode and the high-voltage electrode longer than the discharge initiation distance, since the downstream section of the dielectric tube (i.e. the portion closer to the charge-collecting section) is more likely to undergo internal contamination and degradation due to the influence of the sample introduced into the charge-collecting section and other factors. Confining the electric discharge to the upstream section where such contamination and degradation do not easily develop will more effectively prevent destabilization of the detection signal or an increase in the amount of noise due to the contamination or degradation.

Accordingly, the dielectric barrier discharge ionization detector according to the present invention may preferably have the two ground electrodes arranged so that the distance between the ground electrode located in the upstream section of the gas passage and the high-voltage electrode is shorter than the discharge initiation distance, while the distance between the ground electrode located in the downstream section of the gas passage and the high-voltage electrode is longer than the discharge initiation distance.

Advantageous Effects of the Invention

As described to this point, in the dielectric barrier discharge ionization detector according to the present invention, the fluctuation of the occurrence location of the electric discharge is prevented and the stability of the detection output is improved in a BID having a configuration in which a high-voltage electrode and two ground electrodes are circumferentially formed on the outer circumferential surface of a dielectric tube, with the high-voltage electrode located between the ground electrodes.

DESCRIPTION OF EMBODIMENTS

Modes for carrying out the present invention are hereinafter described using an embodiment.

Embodiment

Figure 1:
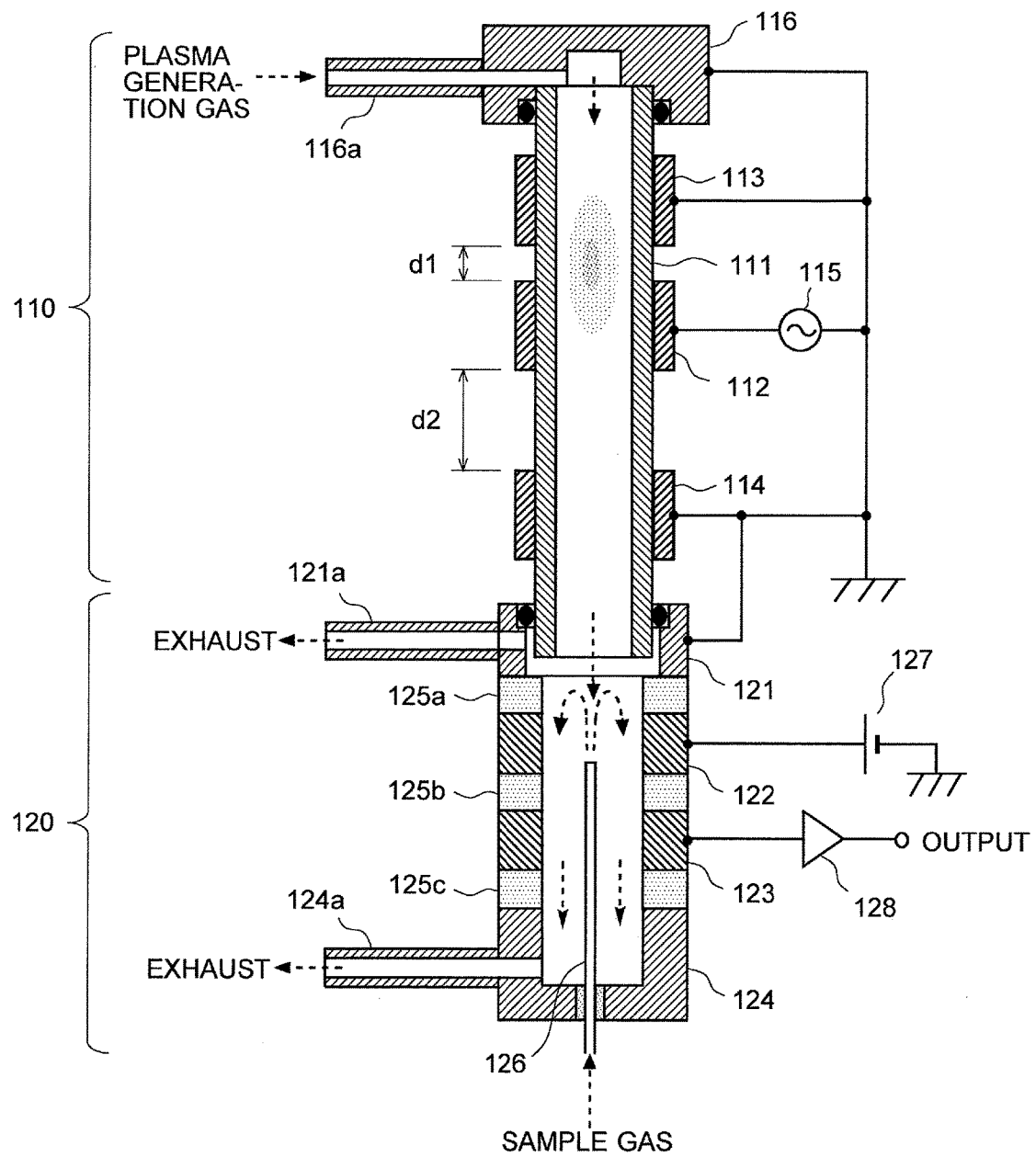
FIG. 1 is a schematic configuration diagram of a BID according to one embodiment of the present invention.

FIG. 1 is a schematic configuration diagram of a BID according to one embodiment of the present invention.

The BID of the present embodiment includes a cylindrical dielectric tube 111 through which a plasma generation gas is passed. In the following description, for convenience of explanation, the vertical direction is defined in such a manner that the upstream side in the flow direction of the gas (indicated by the downward arrows in FIG. 1) in the cylindrical dielectric tube 111 is called the "upper" side, and the downstream side is called the "lower" side. However, this definition does not limit the direction in which the BID should be used.

On the outer wall surface of the cylindrical dielectric tube 111, three ring-shaped electrodes made of a conductor, such as stainless steel or copper, are arranged along the gas flow direction.

Among the three electrodes, the central electrode 112 has a high AC excitation voltage power source 115 connected, while the two electrodes 113 and 114 located above and below the electrode 112 are both grounded. Hereinafter, the electrodes 112, 113 and 114 are called the "high-voltage electrode", "upstream-side ground electrode" and "downstream-side ground electrode", respectively, and these electrodes are collectively called the "plasma generation electrodes". The high AC excitation voltage power source 115 generates a high AC voltage at a frequency within a range of 1 kHz-100 kHz, more preferably, approximately 5 kHz-30 kHz (low frequency), with an amplitude of approximately 5 kV-10 kV. The AC voltage may have any waveform, such as a sinusoidal, rectangular, triangular or sawtooth wave.

In the BID of the present embodiment, the area above the lower end of the downstream-side ground electrode 114 in FIG. 1 is the discharging section 110, and the area below the lower end of the downstream-side ground electrode 114 is the charge-collecting section 120.

The cylindrical dielectric tube 111 has a tube-line tip member 116 at its upper end, to which a gas supply tube 116a is connected. Through this gas supply tube 116a, a plasma generation gas (Ar, He or similar inert gas) doubling as a dilution gas is supplied into the cylindrical dielectric tube 111. Since the wall surface of the cylindrical dielectric tube 111 is present between the plasma generation gas and each of the plasma generation electrodes 112, 113 and 114, the wall surface itself functions as the dielectric coating layer which covers the surfaces of the plasma generation electrodes 112, 113 and 114, enabling dielectric barrier discharge to occur, as will be described later.

On the downstream side of the cylindrical dielectric tube 111, a connection member 121, bias electrode 122 and collecting electrode 123, all of which are cylindrical bodies having the same inner diameter, are arranged along the gas flow direction, with insulators 125a and 125b made of alumina, PTFE resin or similar material inserted in between. On the downstream side of the collecting electrode 123, a tube-line end member 124 in the form of a cylindrical body with a closed bottom is attached via an insulator 125c. The inner space formed by the connection member 121, bias electrode 122, collecting electrode 123, tube-line end member 124 and insulators 125a, 125b and 125c communicates with the inner space of the cylindrical dielectric tube 111.

A bypass exhaust tube 121a for exhausting a portion of the plasma generation gas to the outside is connected to the circumferential surface of the connection member 121. A sample exhaust tube 124a is connected to the circumferential surface of the tube-line end member 124. A thin sample introduction tube 126 is inserted through the bottom of the tube-line end member 124. Through this sample introduction tube 126, a sample gas is supplied into the charge-collecting section 120. The charge-collecting section 120 is heated to a maximum temperature of approximately 450° C. by an external heater (not shown) in order to maintain the sample gas in the gasified state.

The connection member 121 is grounded and functions as a recoil electrode for preventing charged particles in the plasma carried by the gas stream from reaching the collecting electrode 123. The bias electrode 122 is connected to a bias DC power source 127. The collecting electrode 123 is connected to a current amplifier 128.

The operation for detecting a sample component contained in a sample gas in the present BID is hereinafter schematically described. As indicated by the rightward arrow in FIG. 1, a plasma generation gas doubling as a dilution gas is supplied through the gas supply tube 116a into the cylindrical dielectric tube ill. The plasma generation gas flows downward through the cylindrical dielectric tube 111, a portion of which is exhausted through the bypass exhaust tube 121a to the outside, while the remaining portion serving as the dilution gas flows downward through the charge-collecting section 120, to be exhausted through the sample exhaust tube 124a to the outside. Meanwhile, the sample gas containing the sample component is supplied through the sample introduction tube 126 and ejected from the sample-gas ejection port at the end of the same tube into the charge-collecting section 120. Although the direction in which the sample gas is ejected from the sample-gas ejection port is opposite to the flow direction of the dilution gas, the sample gas is immediately pushed backward, being merged with the dilution gas and flowing downward, as indicated by the arrows in FIG. 1.

As noted earlier, while the plasma generation gas is flowing through the cylindrical dielectric tube 111, the high AC excitation voltage power source 115 applies a high AC voltage between the high-voltage electrode 112 and the upstream-side ground electrode 113 as well as between the high-voltage electrode 112 and the downstream-side ground electrode 114. As a result, a dielectric barrier discharge occurs within the cylindrical dielectric tube 111, whereby the plasma generation gas is ionized and a cloud of plasma (atmospheric-pressure non-equilibrium plasma) is generated. The excitation light emitted from the atmospheric-pressure non-equilibrium plasma travels through the discharging section 110 and the charge-collecting section 120 to the region where the sample gas is present, and ionizes the sample component in the sample gas. The thereby generated ions move toward the collecting electrode 123 due to the effect of the electric field created by the DC voltage applied to the bias electrode 122. Upon reaching the collecting electrode 123, the ions give electrons to or receive electrons from the same electrode. Consequently, an ion current corresponding to the amount of ions generated from the sample component by the action of the excitation light, i.e.

an ion current corresponding to the amount of sample component, is fed to the current amplifier 128. The current amplifier 128 amplifies this current and produces a detection signal. In this manner, the BID according to the present embodiment produces a detection signal corresponding to the amount (concentration) of the sample component contained in the sample gas introduced through the sample introduction tube 126.

The basic components of the BID in the present embodiment are the same as those of commonly used BIDs. The previously described basic operation for detection is also similar to that of commonly used BIDs. The structural characteristic of the BID according to the present embodiment exists in that the distance between the high-voltage electrode 112 and the upstream-side ground electrode 113 (which is hereinafter called the "upstream-side inter-electrode distance") d1 is shorter than the discharge initiation distance between these two electrodes, whereas the distance between the high-voltage electrode 112 and the downstream-side ground electrode 114 (which is hereinafter called the "downstream-side inter-electrode distance") d2 is longer than the discharge initiation distance between these two electrodes. The discharge initiation distance depends on such parameters as the frequency and amplitude of the low-frequency AC voltage, waveform of the power source, kind and concentration of the plasma generation gas, as well as the material of the cylindrical dielectric tube 111. Accordingly, each of the upstream and downstream-side inter-electrode distances d1 and d2 should be appropriately adjusted according to those parameters.

The previously described configuration in which the upstream-side inter-electrode distance d1 is shorter than the discharge initiation distance while the downstream-side inter-electrode distance d2 is longer than the discharge initiation distance allows an electric discharge to occur only within the space between the high-voltage electrode 112 and the upstream-side ground electrode 113 when the low-frequency high AC voltage from the high AC excitation voltage power source 115 is applied between the high-voltage electrode 112 and the upstream-side ground electrode 113 as well as between the high-voltage electrode 112 and the downstream-side ground electrode 114. As a result, the positional fluctuation of the plasma generation area within the cylindrical dielectric tube 111 is prevented, so that the detection signal produced by the current amplifier 128 maintains a stable baseline.

Test Example

Figure 2:
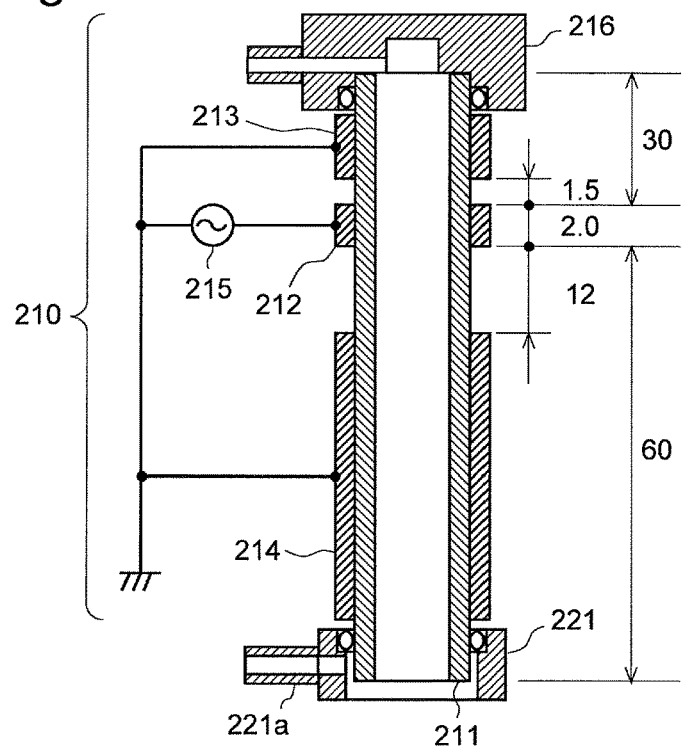
FIG. 2 is a diagram showing the electrode arrangement in a test example.
Figure 3:
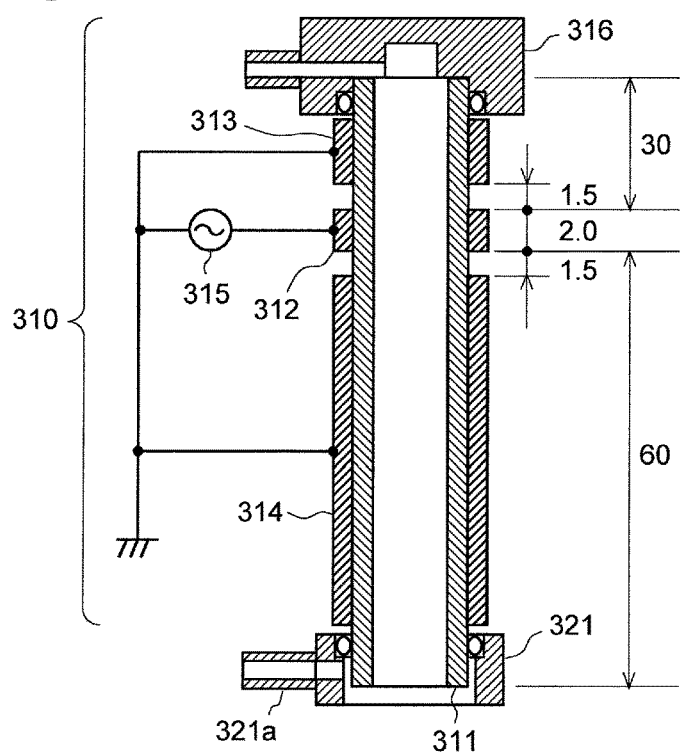
FIG. 3 is a diagram showing the electrode arrangement in a comparative example.

Hereinafter described is a test conducted for confirming the effect of the BID according to the present embodiment. The test was performed using a BID in which the upstream-side inter-electrode distance d1 was shorter than the discharge initiation distance and the downstream-side inter-electrode distance d2 was longer than the discharge initiation distance (this BID is hereinafter called the "test example") as well as a BID in which both of the inter-electrode distances d1 and d2 were shorter than the discharge initiation distance (this BID is hereinafter called the "comparative example"). FIG. 2 shows the electrode arrangement of the discharging section in the test example, while FIG. 3 shows that of the discharging section in the comparative example. In both of FIGS. 2 and 3, the components which have corresponding counterparts in FIG. 1 are denoted by numerals whose last two digits are the same as those of their respective counterparts. Sections other than the discharging section have similar configurations to FIG. 1 and are therefore omitted from those figures. In both of the test and comparative examples, the cylindrical dielectric tubes 211 and 311 were quartz tubes measuring 4 mm in outer diameter, 2 mm in inner diameter and 92 mm in length. Strips of copper foil were wound on the outer circumferential surface of each of the cylindrical dielectric tubes 211 and 311 to form the high-voltage electrode 212 or 312, upstream-side ground electrode 213 or 313 as well as downstream-side ground electrode 214 or 314. In both of the test and comparative examples, the high-voltage electrodes 212 and 312 were 2 mm in length, and the upstream-side inter-electrode distance (d1) was 1.5 mm. The difference between the test and comparative examples existed in the downstream-side inter-electrode distance (d2), which was 12 mm in the test example and 1.5 mm in the comparative example. Those values of the inter-electrode distance were previously determined by experiments. That is to say, it had been confirmed beforehand that, when the distance between the high-voltage electrode 212 or 312 and each ground electrode 213, 214, 313 or 314 was 1.5 mm, an electric discharge would occur between the two electrodes (i.e. 1.5 mm was shorter than the discharge initiation distance). Similarly, it had been confirmed beforehand that no electric discharge would occur between two electrodes when the distance between the high-voltage electrode 212 or 312 and each ground electrode 213, 214, 313 or 314 was 12 mm (i.e. 12 mm was longer than the discharge initiation distance).

It should be noted that, in both of the test and comparative examples, the downstream-side ground electrode 214 or 314 of the BID was made to be longer than those of conventional BIDs (see FIGS. 2 and 3). This design was adopted in order to prevent a creeping discharge between the high-voltage electrode 212 or 312 and the connection member 221 or 321 attached to the lower portion of the cylindrical dielectric tube 211 or 311. This design is not directly related to the present invention, and therefore, will not be described in detail.

Figure 4:
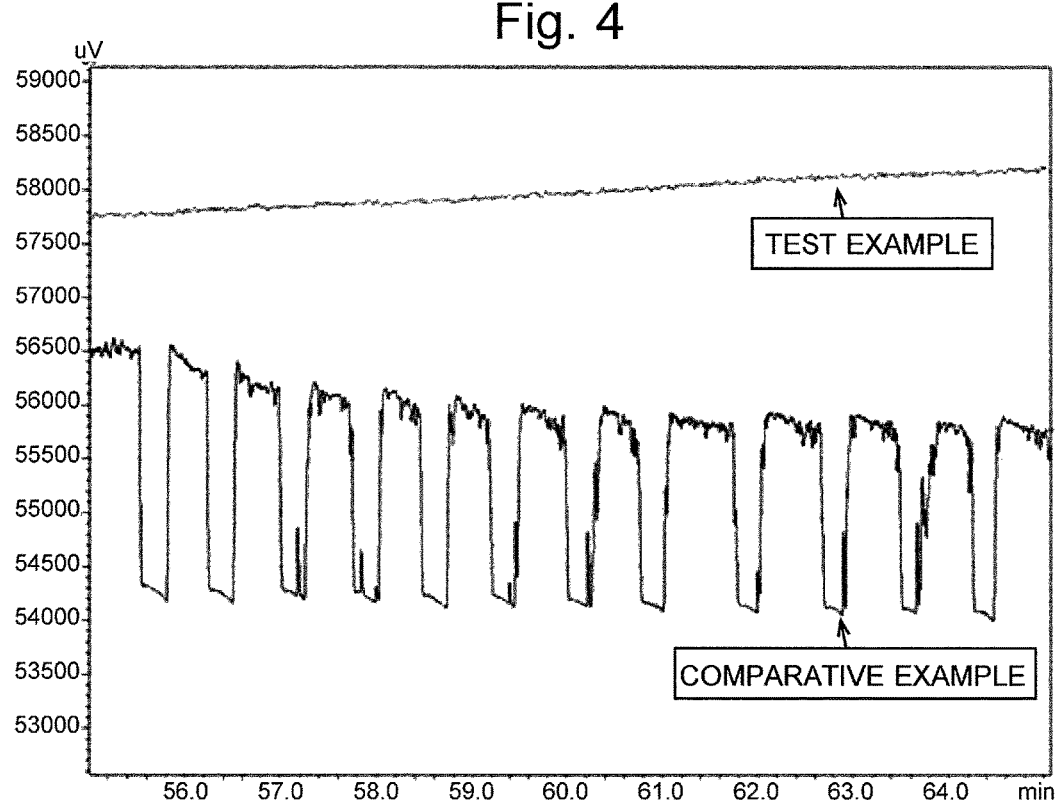
FIG. 4 is a graph showing the output baseline in the test example and the comparative example.

In each of the aforementioned BIDs, while Ar gas (with a degree of purity of 99.9999% or higher) was continuously introduced as the plasma generation gas with no introduction of the sample, the high AC excitation voltage power source 215 or 315 was energized to apply an AC high voltage having a sinusoidal current waveform at a frequency of approximately 40 kHz with a voltage amplitude of approximately 5 kVp-p, and the output of the current amplifier (numeral 128 in FIG. 1) was measured. FIG. 4 shows the measured results.

Figure 8:
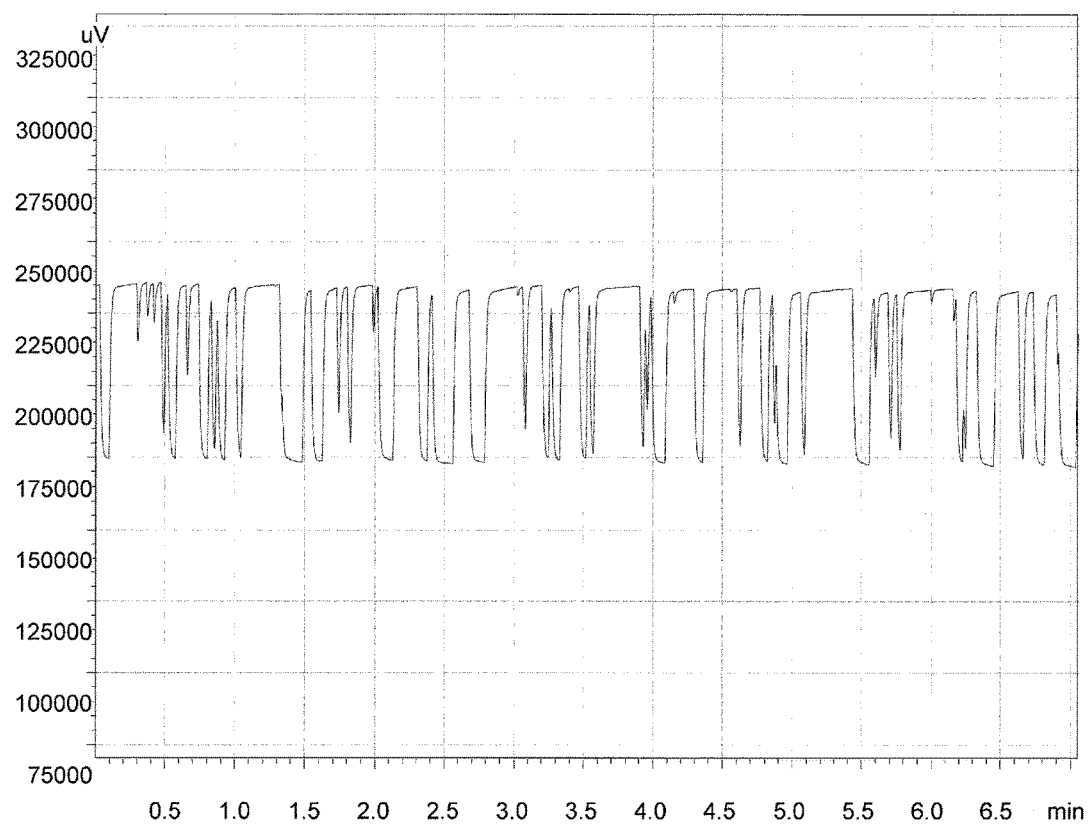
FIG. 8 is a graph showing an output baseline recorded when the output was unstable in a conventional BID.

As is evident from FIG. 4, a stable baseline was obtained in the test example. By comparison, in the comparative example, the stable state did not last long and an unstable state similar to the one shown in FIG. 8 occurred.

Figure 5:
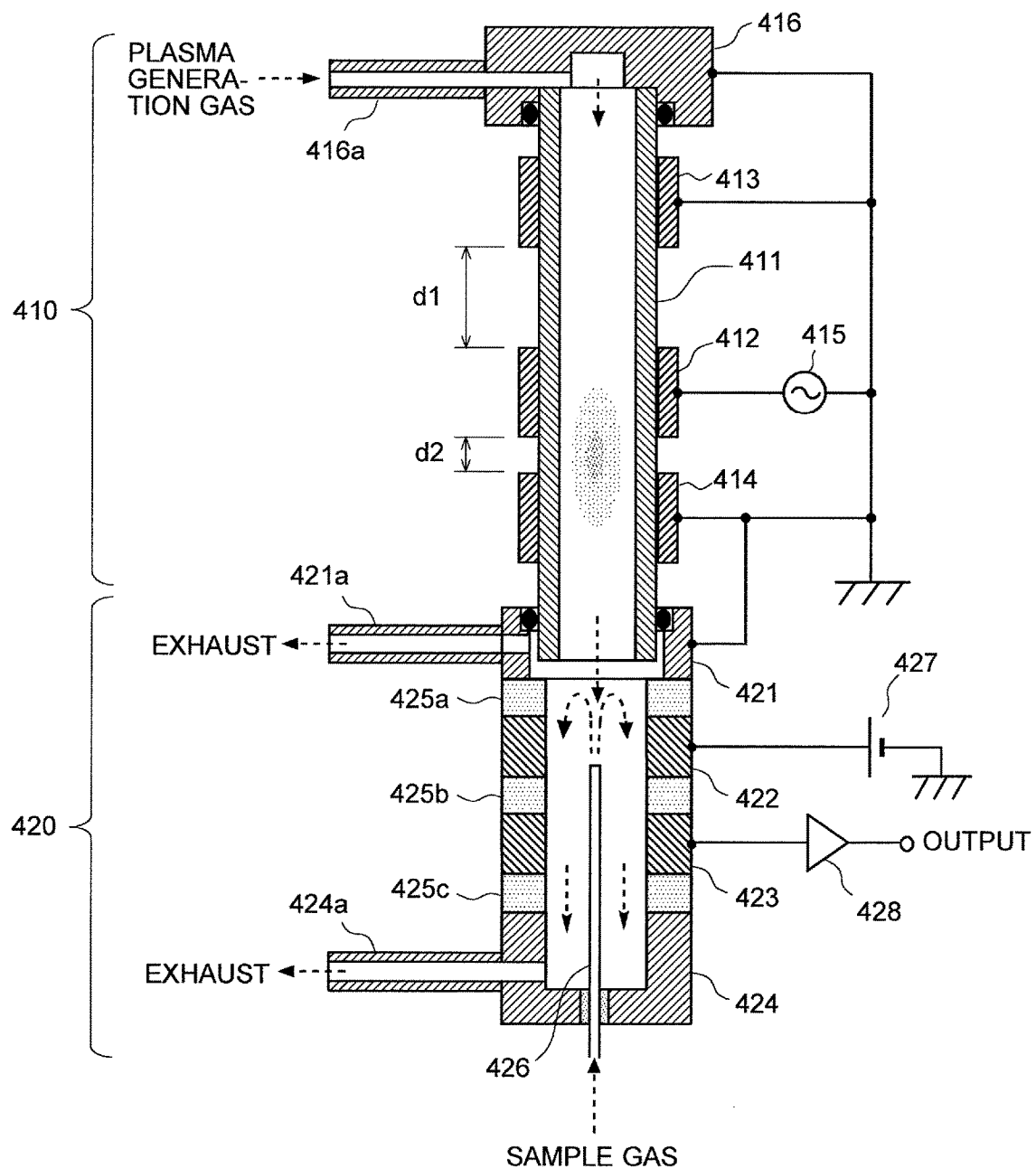
FIG. 5 is a diagram showing another configuration example of the BID according to the present invention.

A mode for carrying out the present invention has been described thus far using an embodiment. The present invention is not limited to the previous embodiment and can be appropriately modified within the gist of the present invention. For example, as opposed to FIG. 1 in which the upstream-side inter-electrode distance d1 is short and the downstream-side inter-electrode distance d2 is long, those distances may be changed as shown in FIG. 5, in which the upstream-side inter-electrode distance d1 is long and the downstream-side inter-electrode distance d2 is short (in FIG. 5, the components which have corresponding counterparts in FIG. 1 are denoted by numerals whose last two digits are the same as those of their respective counterparts). In this case, each of the inter-electrode distances d1 and d2 should be adjusted according to such parameters as the frequency and amplitude of the AC voltage applied by the high AC excitation voltage power source 415, kind and concentration of the plasma generation gas, as well as the dielectric material forming the cylindrical dielectric tube 411 so that the electric discharge within the cylindrical dielectric tube 411 will be confined to the area between the high-voltage electrode 412 and the downstream-side ground electrode 414.

Figure 6:
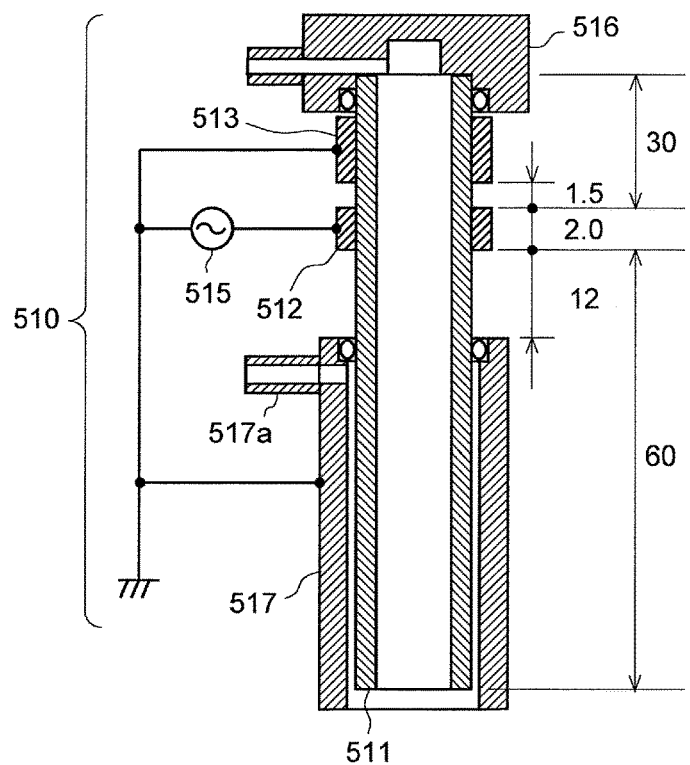
FIG. 6 is a diagram showing still another configuration example of the BID according to the present invention.
Figure 7:
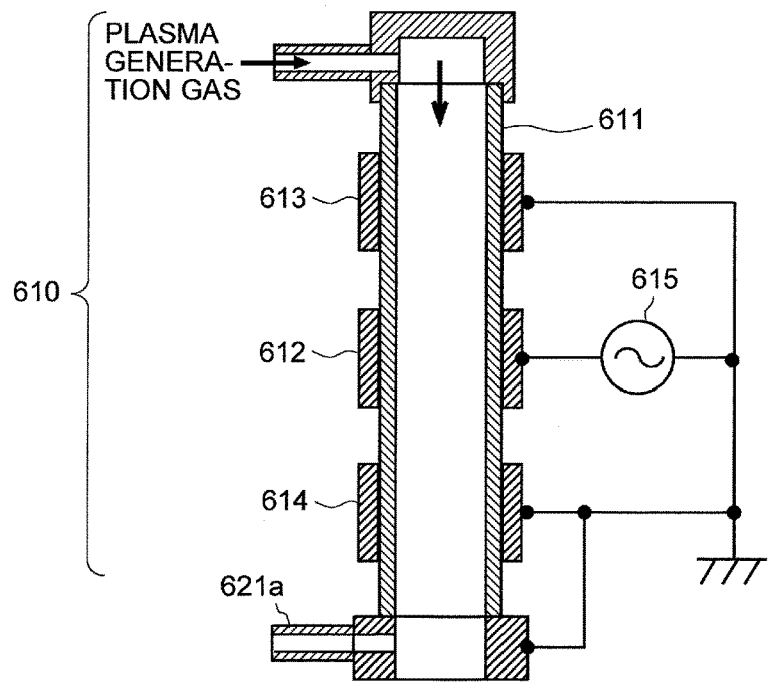
FIG. 7 is a schematic configuration diagram of the discharging section and surrounding area in a conventional BID.

In the BID according to the present invention, the connection member which connects the dielectric tube to the charge-collecting section may be combined with the downstream-side ground electrode into a single component. FIG. 6 shows one example of the BID having such a configuration (in FIG. 6, the components which have identical or corresponding counterparts in FIG. 2 are denoted by numerals whose last two digits are the same as those of their respective counterparts, and their descriptions will be appropriately omitted). The BID in FIG. 6 corresponds to the configuration obtained by removing the downstream-side ground electrode 214 from FIG. 2 and extending the connection member 221 over the area where the downstream-side ground electrode 214 was previously provided. This member in FIG. 6 which corresponds to the extended connection member 221 is hereinafter called the "tubular member 517". The tubular member 517 is electrically grounded, has a bypass exhaust tube 517a connected to its circumferential surface, and surrounds the outer circumferential surface of the cylindrical dielectric tube 511, leaving a narrow gap in between for allowing a passage of gas. With such a configuration, the tubular member 517 can fulfill the functions of both the connection member and the downstream-side ground electrode. In the example of FIG. 6, the distance between the high-voltage electrode 512 and the upstream-side ground electrode 513 is shorter than the discharge initiation distance between these two electrodes, while the distance the high-voltage electrode 512 and the tubular member (downstream-side ground electrode) 517 is longer than the discharge initiation distance between these two elements. Therefore, when the high voltage power source 515 is energized, an electric discharge occurs within the space between the high-voltage electrode 512 and the upstream-side ground electrode 513, while the tubular member 517 serves to prevent the generation area of the plasma by the electric discharge from spreading into the downstream region. It should be noted that the dimensions (in mm) shown in FIG. 6 are mere examples and are not intended to limit the present invention. For example, it is possible to make the distance between the high-voltage electrode 512 and the upstream-side ground electrode 513 longer than the discharge initiation distance between these two electrodes, and to make the distance between the high-voltage electrode 512 and the tubular member 517 shorter than the discharge initiation distance between these two elements. In this case, the electric discharge occurs within the space between the high-voltage electrode 512 and the tubular member 517, while the upstream-side ground electrode 513 serves to prevent the generation area of the plasma by the electric discharge from spreading into the upstream region.

REFERENCE SIGNS LIST 110, 410 . . . Discharging Section
111, 411 . . . Cylindrical Dielectric Tube
112, 412 . . . High-Voltage Electrode
113, 413 . . . Upstream-Side Ground Electrode
114, 414 . . . Downstream-Side Ground Electrode
115, 415 . . . High AC Excitation Voltage Power Source
120, 420 . . . Charge-Collecting Section
122, 422 . . . Bias Electrode
123, 423 . . . Collecting Electrode
126, 426 . . . Sample Introduction Tube
127, 427 . . . Bias DC Power Source
128, 428 . . . Current Amplifier
d1 . . . Upstream-Side Inter-Electrode Distance
d2 . . . Downstream-Side Inter-Electrode Distance

The invention claimed is:

1. A dielectric barrier discharge ionization detector, comprising:
  a) a dielectric tube containing one section of a gas passage through which a plasma generation gas is passed;
  b) a high-voltage electrode circumferentially formed on an outer wall of the dielectric tube;
  c) two ground electrodes electrically grounded and circumferentially formed on the outer wall of the dielectric tube at positions between which the high-voltage electrode is located;
  d) a voltage supplier connected to the high-voltage electrode, for applying an AC voltage between the high-voltage electrode and each of the two ground electrodes so as to generate an electric discharge within the dielectric tube and thereby generate plasma from the plasma generation gas; and
  e) a charge-collecting section forming a section of the gas passage located downstream of a generation area of the plasma, including a sample-gas introducer for introducing a sample gas into the downstream section and a collecting electrode for collecting ions generated from a sample component in the sample gas by light emitted from the plasma,
  wherein a distance between one ground electrode of the two ground electrodes and the high-voltage electrode is different from a distance between the other ground electrode and the high-voltage electrode.

2. The dielectric barrier discharge ionization detector according to claim 1, wherein the two ground electrodes are arranged so that the distance between the ground electrode located in an upstream section of the gas passage and the high-voltage electrode is shorter than the distance between the ground electrode located in a downstream section of the gas passage and the high-voltage electrode.

3. The dielectric barrier discharge ionization detector according to claim 1, wherein the plasma generation gas is argon gas.

4. The dielectric barrier discharge ionization detector according to claim 2, wherein the plasma generation gas is argon gas.

* * * * *